United States Patent [19]

Hafner et al.

[11] Patent Number: 4,948,780
[45] Date of Patent: Aug. 14, 1990

[54] ALCOHOLS AND ETHERS HAVING CYCLODODECYL AND CYCLODODECENYL GROUPS, PROCESS FOR THEIR PREPARATION AND SCENTS CONTAINING SAME

[75] Inventors: Walter Hafner, Eurasburg; Helmut Gebauer, Munich; Erich Markl, Munich; Marlies Regiert, Munich, all of Fed. Rep. of Germany

[73] Assignee: Consortium fur Elektrochemische Industrie GmbH, Munich, Fed. Rep. of Germany

[21] Appl. No.: 141,127

[22] Filed: Jan. 6, 1988

[30] Foreign Application Priority Data

Feb. 6, 1987 [DE] Fed. Rep. of Germany ....... 3703585

[51] Int. Cl.$^5$ .............................................. A61K 7/46
[52] U.S. Cl. ........................................ 512/8; 568/667; 568/579; 568/821
[58] Field of Search .................... 512/8; 568/667, 579, 568/821

[56] References Cited

U.S. PATENT DOCUMENTS

| | | | |
|---|---|---|---|
| 3,281,474 | 10/1966 | Holzminden | 568/579 |
| 3,845,141 | 10/1974 | Naegeli | 568/579 |
| 4,301,303 | 11/1981 | Hoffmann et al. | 568/821 |
| 4,359,588 | 11/1982 | Burzin et al. | 568/579 |
| 4,506,102 | 3/1985 | Kaufhold et al. | 568/667 |
| 4,601,851 | 7/1986 | Bartmann et al. | 568/667 |

FOREIGN PATENT DOCUMENTS

| | | | |
|---|---|---|---|
| 22462 | 1/1981 | European Pat. Off. | 512/8 |
| 2152016 | 5/1972 | Fed. Rep. of Germany | 568/579 |
| 2852344 | 6/1980 | Fed. Rep. of Germany | 568/821 |

Primary Examiner—James H. Reamer
Attorney, Agent, or Firm—Collard, Roe & Galgano

[57] ABSTRACT

Compounds of the general formulae

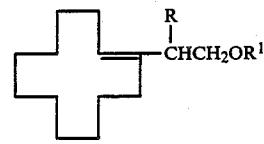

(I)

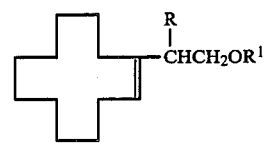

(II)

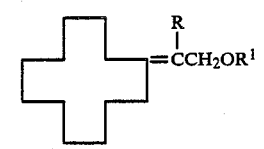

(III)

and

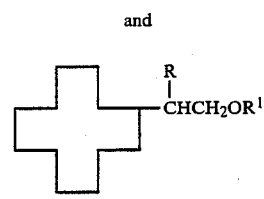

(IV)

in which R may be a methyl or ethyl radical and $R^1$ may be a hydrogen, methyl or ethyl radical are disclosed. Also provided as part of the present invention are processes for the preparation of the above compounds. The compounds of the invention are useful as scents.

2 Claims, No Drawings

ALCOHOLS AND ETHERS HAVING CYCLODODECYL AND CYCLODODECENYL GROUPS, PROCESS FOR THEIR PREPARATION AND SCENTS CONTAINING SAME

The present invention relates to novel alcohols and ethers having cyclododecyl and cyclododecenyl groups. More particularly, the present invention relates to such compounds useful as scents or fragrant substances and a process for their preparation.

Numerous scents having cyclododecyl and cyclododecenyl groups are known. These are mainly ethers and ketones, but also include alcohol, ester or nitrile derivatives. In general, these compounds belong to the group comprising the wood scents, however, each compound has its own character or note.

It is, therefore, an object of the present invention to provide novel wood scents having a unique character and which exhibit good adherency, a low threshold and a low dilution limit.

The foregoing and related objects are achieved by the compounds of the present invention, wherein such compounds have the general formulae of

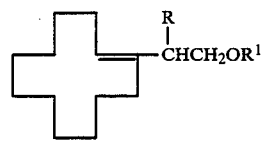
(I)

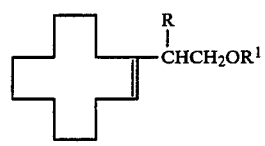
(II)

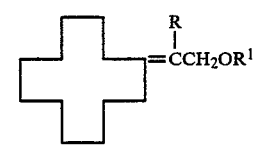
(III)

and

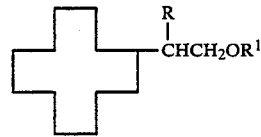
(IV)

wherein R may be a methyl or ethyl radical and $R^1$ may be a hydrogen, methyl or ethyl radical.

A process for the preparation of compounds of the general formulae

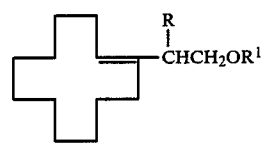
(I)

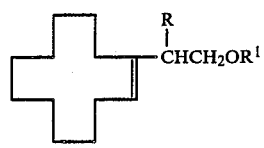
(II)

and

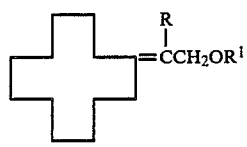
(III)

wherein R may be a methyl or ethyl radical and $R^1$ may be a hydrogen, methyl or ethyl radical, comprises the steps of:

(a) reacting cyclododecanone with Br—CHR—COOEt (R has the above-mentioned meaning) in the presence of zinc and, when the elimination of water is complete, (b) reducing the reaction product from (a) using lithium aluminum hydride and, optionally, etherifying the product in a conventionally known manner.

Cyclododecanone and Br-CHR-COOEt (R as defined above) are either commercially available compounds or are easily accessible by simple known processes. The invention reaction preferably takes place at temperatures in the range from 80 to 110° C. in inert organic solvents which are customary for Reformatski reactions, such as, aromatics, for example toluene, and ethers, for example, diethyl ether Vigorous stirring, and also, optionally, the use of ultrasound, promote the reaction. After decomposition using mineral acids, such as hydrochloric acid, water elimination takes place using acids such as phosphoric acid or toluenesulfonic acid, optionally, with the aid of an esterification reagent such as acetic anhydride. The reaction product from (a) is reduced using lithium aluminum hydride. For each radical, R, mixtures of isomers comprising the particular compounds of the general formulae I, II and/or III are obtained, which can be resolved, for example, by fractional distillation, freezing out or chromatographic methods. The composition of the mixtures of isomers depends substantially on the reaction and work-up conditions selected in the synthesis.

A process for the preparation of compounds of the general formula

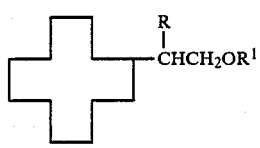
(IV)

wherein,

R may be a methyl or ethyl radical, and $R^1$ may be a hydrogen, methyl or ethyl radical, comprises the steps of:

reacting the reaction product from (a) or (b) with a reduction catalyst and hydrogen and, optionally, etherifying this reaction product in a conventionally known manner.

The reduction catalysts used are, preferably, palladium on activated charcoal or Raney nickel.

The alcohols according to the invention can be converted into the methyl or ethyl ethers, which are likewise wood scents, by known processes, for example, the Williamson ether synthesis.

The invention will now be described in further detail with reference being made to the following examples. It should, however, be recognized that the examples are given as being illustrative of the present invention and are not intended to define the spirit and scope thereof.

EXAMPLE 1

2-Cyclododecenylpropan-1-ols 150 ml of toluene and 128 g of granulated zinc are introduced into a 2-liter three-neck flask equipped with magnetic stirrer, thermometer, reflux condenser and dropping funnel with an inert gas connection. The mixture was then warmed to 95° C. under argon. A mixture of 334 g of cyclododecanone, 330 g of ethyl bromopropionate, 350 ml of toluene and 50 ml of ether was added dropwise over the course of one hour. The temperature was kept at 95–100° C. for 4 hours. After cooling, the batch was poured onto ice and acidified using concentrated hydrochloric acid and the layers were separated. The aqueous phase was extracted by shaking once with 200 ml of tert.-butyl methyl ether and then discarded. The solvents were substantially removed from the combined organic layers by distillation. 300 ml of xylene, 210 g of acetic anhydride and 5 g of p-toluenesulfonic acid were added to the residue and the mixture was refluxed for 3 hours. 5 g of sodium carbonate were then carefully added, the acetic acid, acetic anhydride and solvents were removed by distillation in a partial vacuum when the gas evolution had subsided, and the residue was filtered. The distillation was subsequently continued in vacuo. After a preliminary fraction, 390 g of a mixture of isomers of ethyl 2-cyclododecenylpropionate were passed over at 95–115° C./0.1–0.3 mbar.

200 g of this mixture of isomers were added dropwise to a solution or suspension of 20 g of lithium aluminum hydride in 400 ml of tetrahydrofuran under argon at 30–40° C. The mixture was kept at this temperature for 2 hours and at 65° C. for a further 4 hours. After cooling, the batch was poured onto ice and acidified using hydrochloric acid, and the upper layer was separated off. The aqueous phase was extracted by shaking once with tert.-butyl methyl ether and discarded. The combined organic layers were washed by shaking with dilute sodium carbonate solution, dried over solid $K_2CO_3$ and distilled via a Vigreux column. 160 g of a mixture of isomers (boiling point 103° C. at 0.07 mbar) were obtained having the following composition: 90% by weight of the compound of the general formula I, 9% by weight of the compound of the general formula II and less than 1% by weight of the compound of the general formula III, where $R=CH_3$ and $R^1=H$.

Aroma character: Strongly amber-scented wood with flowery aspects of lily of the valley.

EXAMPLE 2

2-Cyclododecenylpropyl methyl ether 15 g of the compound prepared according to Example 1 were added to a suspension of 4.4 g of sodium hydride in 150 ml of dry tetrahydrofuran while flushing with argon. The mixture was then refluxed for 2 hours. 8.5 g of dimethyl sulfate in 50 ml of tetrahydrofuran were then added, and the mixture was refluxed for a further hour. The batch was then poured onto ice, and the organic material was taken up in tert.-butyl methyl ether and extracted by shaking with 10% strength NaOH. After drying using $K_2CO_3$, the solvents were removed and the product was distilled via a small Vigreux column.

10 g of cyclododecenylpropyl methyl ether (boiling point 90–97° C./0.2 mbar) were obtained.

Aroma character: woody, flowery, amber-scented, earthy, reminiscent of vetiver oil.

EXAMPLE 3

2-Cyclododecylpropan-1-ol 45 g of the mixture of isomers of 2-cyclododecenylpropan-1-ol from Example 1 were heated for 7 hours at 200° with 2 g of Raney nickel and 10 ml of ethanol in a shaken autoclave with 200 bar of hydrogen. After removal of catalyst and solvent, the reaction mixture was distilled. At 105–110° C. and 0.7 mbar, 35 g of 2-cyclododecylpropan-1-ol were obtained.

Aroma character: somewhat flowery, warm, strong wood scent.

EXAMPLE 4

2-Cyclododecylpropyl ethyl ether 15 g of 2-cyclododecylpropan-1-ol were stirred with 4 g of sodium hydride in 150 ml of tetrahydrofuran for two hours at the boiling temperature excluding air. 6 g of diethyl sulfate were then added dropwise, and the mixture was refluxed for a further two hours. The cooled reaction mixture was poured onto ice and extracted by stirring with 20 ml of 10% strength NaOH and 50 ml of tert.-butyl methyl ether. The aqueous layer was again extracted by shaking with tert.-butyl methyl ether, and the combined organic layers were again extracted by shaking with 10% strength NaOH and distilled. After removal of the solvents, 9.5 g of 2-cyclododecylpropyl ethyl ether were obtained at 92–95° C. and 0.2 mbar.

Aroma character: amber-scented, woody, strongly herby, reminiscent of elary sage oil.

EXAMPLE 5

2-Cyclododecenylbutan-1-ols 26 g of zinc powder and 40 ml of dry toluene were heated to 90° C. while excluding air. A mixture of 78 g of ethyl 2-bromobutyrate, 73 g of cyclododecanone, 200 ml of dry toluene and 20 ml of dry diethyl ether was added dropwise over the course of one hour with vigorous stirring. The batch was subsequently stirred for a further 5 hours at 81° C., then cooled and poured into a mixture of ice and hydrochloric acid. The organic layer was separated off and the aqueous layer was extracted by shaking with tert.-butyl methyl ether and discarded. The combined organic layers were again extracted by shaking with dilute hydrochloric acid and water before the solvents were removed by distillation. The residue was heated with 100 ml of mesitylene, 100 ml of acetic anhydride and 2 g of phosphoric acid, acetic acid slowly distilling off. The entire batch was subsequently distilled. 16 g of cyclododecanone were obtained at 95° C./0.1 mbar and 42 g of a mixture of isomers of ethyl 2-cyclododecenylbutyrate were obtained at 95–105° C./0.1 mbar. These 42 g of the mixture of isomers were stirred for 7 hours at 45–50° C. in 150 ml of dry tetrahydrofuran with 3 g of lithium aluminum hydride while excluding air. Decomposition was then effected using ice and hydrochloric acid and the product was taken up in ether, washed until neutral and distilled. After a small preliminary fraction of cyclododecanol, 21 g of 2-cyclododecenylbutan-1-ol were obtained at 115–118° C./0.2 mbar.

Aroma character: Odor of tobacco, cedarleaf oil, wood and ambergris.

While only several embodiments and examples of the present invention have been shown and described, it will be obvious to those skilled in the art that many modifications may be made to the invention without departing from the spirit and scope thereof.

What is claimed is:

1. A compound of a formula selected from the group consisting of:

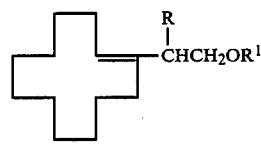
(I)

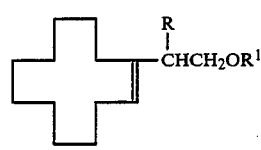
(II)

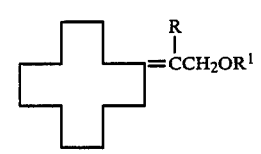
(III)

and

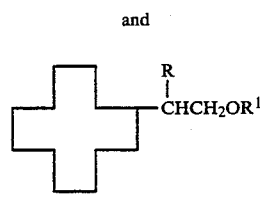
(IV)

wherein:

R is a substituent selected from the group consisting of a methyl group and an ethyl group; and
$R^1$ is a substituent selected from the group consisting of a hydrogen atom, a methyl group and an ethyl group.

2. A composition for use as a scent, comprising:

a compound of a formula selected from the group consisting of:

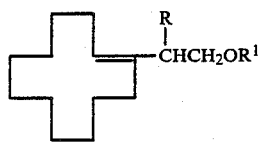
(I)

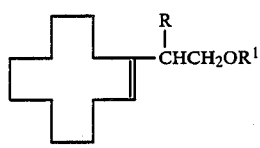
(II)

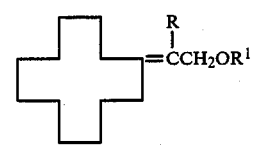
(III)

and

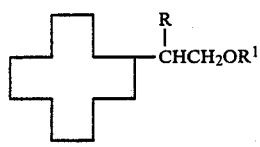
(IV)

wherein,

R is a substituent selected from the group consisting of a methyl group and an ethyl group; and
$R^1$ is a substituent selected from the group consisting of a hydrogen atom, a methyl group and an ethyl group; and a carrier substance.

* * * * *